US00PP30953P3

(12) United States Plant Patent
Ranney

(10) Patent No.: US PP30,953 P3
(45) Date of Patent: Oct. 22, 2019

(54) ***SPIRAEA* PLANT NAMED 'NCSX2'**

(50) Latin Name: ***Spiraea* hybrid**
Varietal Denomination: NCSX2

(71) Applicant: North Carolina State University, Raleigh, NC (US)

(72) Inventor: Thomas Green Ranney, Arden, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 15/932,521

(22) Filed: Mar. 9, 2018

(65) Prior Publication Data

US 2019/0281743 P1 Sep. 12, 2019

(51) Int. Cl.
*A01H 5/00* (2018.01)
*A01H 6/74* (2018.01)

(52) U.S. Cl.
USPC ..... Plt./226

(58) Field of Classification Search
USPC ..... Plt./226
See application file for complete search history.

*Primary Examiner* — Susan McCormick Ewoldt
(74) *Attorney, Agent, or Firm* — Cassandra Bright

(57) ABSTRACT

'NCSX2' is a new cultivar of hybrid *Spiraea* that is a triploid, with red-purple new foliage color, red-purple flowers, and continuous blooming throughout the growing season from May to October. The new variety is a *Spiraea* normally produced as an outdoor garden or container plant.

4 Drawing Sheets

Latin name of the genus and species: *Spiraea* hybrid.
Varietal denomination: 'NCSX2'.

BACKGROUND OF THE INVENTION

The present invention comprises a new and distinct hybrid *Spiraea* cultivar hereinafter referred to by the cultivar name 'NCSX2'. This new *Spiraea* was developed through a breeding program at Mills River, N.C. 'NCSX2' was selected from a population of seedlings grown from a controlled cross of *Spiraea* 'Zelda' (U.S. Plant Pat. No. 21,976 P2, diploid) as the seed parent and *Spiraea japonica* H2007-101-003 (unpatented, tetraploid) as the pollen parent. The first asexual propagation of 'NCSX2' was carried out in July 2012 by rooting stem cuttings at a research nursery in Mills River, N.C. and has been asexually reproduced repeatedly by vegetative cuttings over a 5-year period. 'NCSX2' roots readily from softwood cuttings treated with a basal dip of 4,000 to 5,000 ppm indole butyric acid (potassium salt) in water. 'NCSX2' has been found to retain its distinctive characteristics through successive asexual propagations.

SUMMARY OF THE INVENTION

The following are the unique combination of characteristics of this new cultivar when grown under standard horticultural practices at a research greenhouse in Mills River, N.C.

1. Triploid with a 2C genome size of approximately 0.9 pg.
2. Continuous blooming from May to October.
3. Red-purple flower color and red-purple new foliage color.

CITATIONS

Genome size is further discussed in the following publications, which are incorporated herein by reference: Shearer, K. and T. G. Ranney. 2013. *Ploidy levels and relative genome sizes of species, hybrids, and cultivars of dogwood* (*Corunus* spp.). HortScience 48(7):825-830; Wilson, R. L. and W. A. Hoch. 2009. Identification of sterile, noninvasive cultivars of Japanese spirea. Hortscience 44(7):2031-2034.

COMPARISON TO PARENTAL VARIETIES

'NCSX2' differs from the female parent 'Zelda' in that 'NCSX2' is a triploid, has continuous blooming from May to October, and has red-purple flowers while 'Zelda' is a diploid, is not continuous blooming, and has dark pink-colored flowers. 'NCSX2' differs from the male parent H2007-101-003 in that 'NCSX2' is a triploid, has blooming from May to October, has green foliage color, and has red-purple flowers while H2007-101-003 is a tetraploid, is not continuous blooming, has yellow foliage color, and has pink-colored flowers.

COMPARISON WITH COMMERCIAL CULTIVARS

'NCSX2' is distinguished from most commercial cultivars in that 'NCSX2' is a triploid selection whereas most taxa of *S. japonica* including 'Albiflora' (unpatented), 'Anthony Waterer' (unpatented), 'Candlelight' (unpatented), 'Crispa' (unpatented), 'Dakota Goldcharm®', var. alpina, 'Daphne' (unpatented), 'Darts Red' (unpatented), 'Flaming Mound' (unpatented), 'Flowering Choice' (U.S. Plant Pat. No. 13,916), 'Froebelii' (unpatented), 'Golden Princess' (U.S. Plant Pat. No. 7,537), 'Goldflame' (unpatented), 'Goldmound' (unpatented), 'Gumball' (unpatented), 'Lemon Princess' (unpatented), 'Little Princess' (unpatented), 'Magic Carpet' (U.S. Plant Pat. No. 9,363), 'Neon Flash' (unpatented), 'Norma' (unpatented), and 'Shibori' (unpatented), are diploids while *S. j.* var. *fortunei* is a tetraploid (Wilson and Hoch, 2009). Although 'NCSX2' and 'NCSX1' are both triploids, 'NCSX2' is larger growing (80 to 100 cm high) with Green (137A) mature foliage, and Red-Purple (60C to N57B) upper petal color at anthesis, while 'NCSX1' is smaller growing (46 to 61 cm high), Yellow-Green (145A, 144B, and 144A) mature summer foliage, and Red-Purple (71B) upper petal color at anthesis.

BRIEF DESCRIPTION OF THE DRAWINGS

This new *Spiraea* is illustrated by the accompanying photographs which show the plant's form, foliage and inflorescences at approximately 2 years of age. The colors shown are as true as can be reasonably obtained by conventional photographic procedures. Colors in the photographs may differ slightly from the color values cited in the detailed botanical description, which accurately describe the colors of the new hybrid *Spiraea*.

DETAILED BOTANICAL DESCRIPTION

Figure 1:
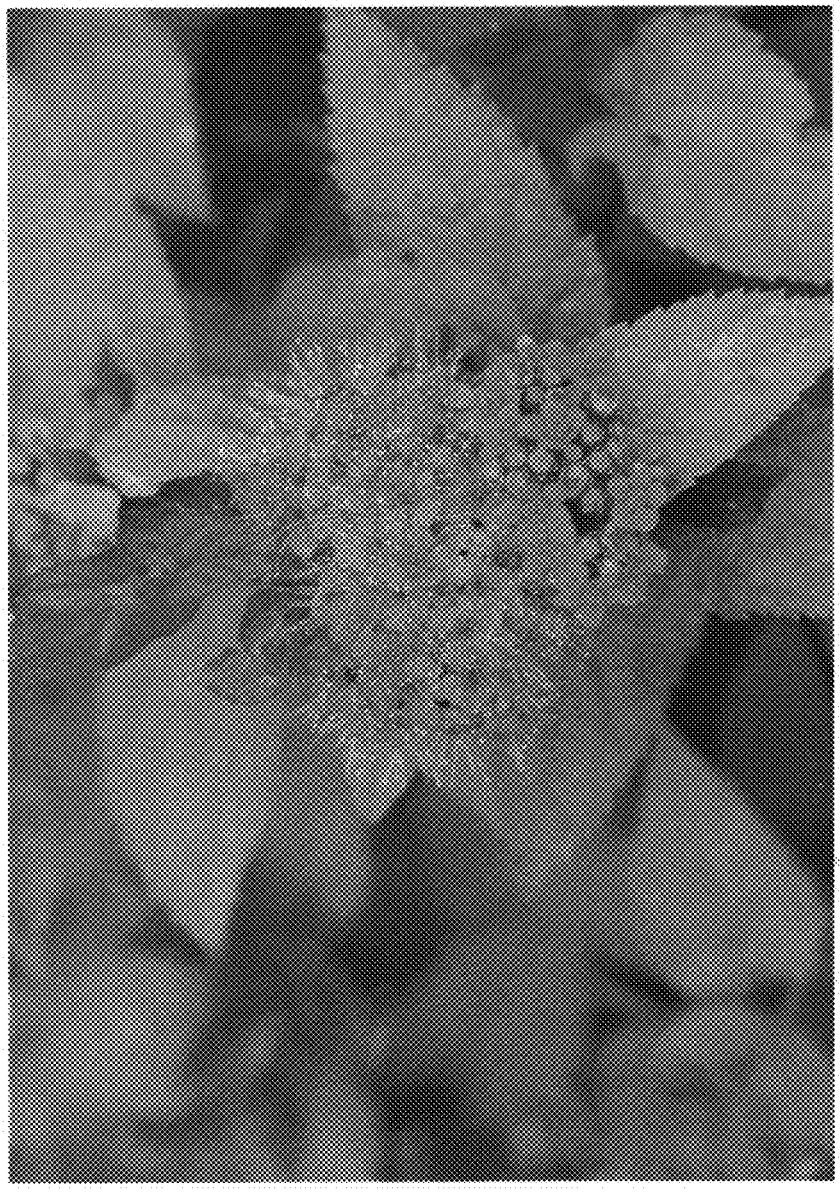
FIG. 1 is a color photograph showing an inflorescence of 'NCSX2' in Mills River, N.C., in the Summer of 2017.
Figure 2:
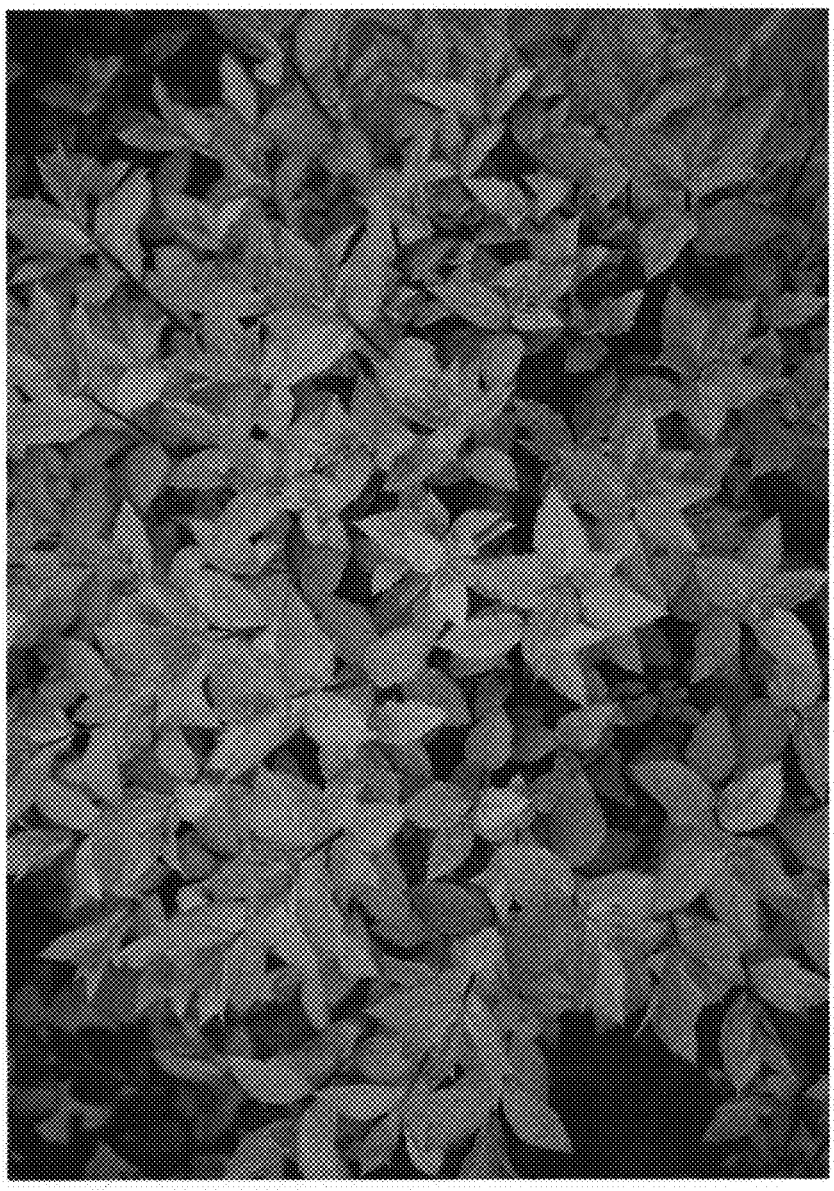
FIG. 2 is a color photograph showing the emerging foliage of 'NCSX2' in Mills River, N.C., in the Spring of 2017
Figure 3:
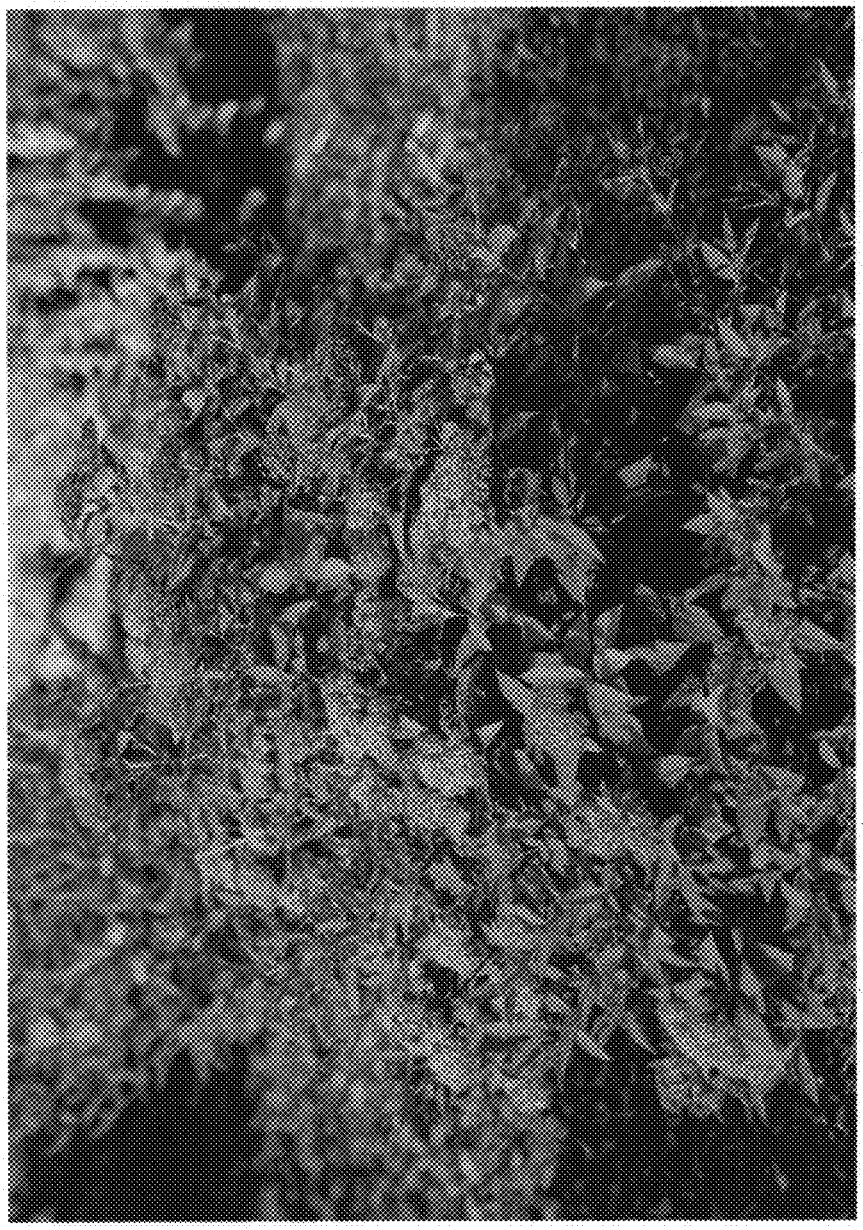
FIG. 3 is a color photograph of the habit of 'NCSX2' in Mills River, N.C., in the Summer of 2017. Flowers are somewhat lighter in color than in FIG. 1 due to sunnier conditions.
Figure 4:
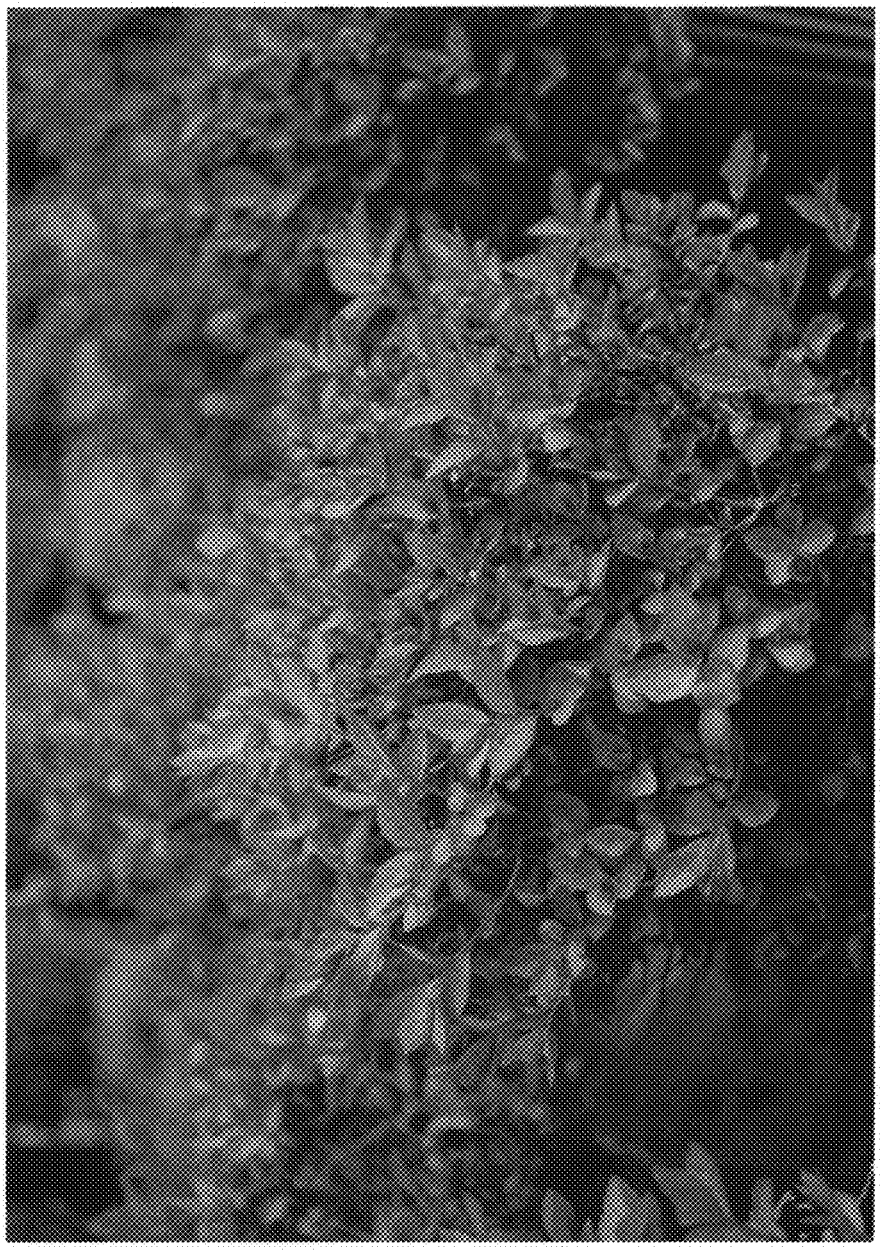
FIG. 4 is a color photograph showing the Fall foliage of 'NCSX2' in Mills River, N.C., in the Fall of 2017

The following is a detailed description of the botanical characteristics of the new and distinct hybrid *Spiraea* known by the denomination. 'NCSX2'. The detailed description was taken on a three-year-old field-grown plant in Mills River, N.C. in 2017, All colors cited herein refer to The Royal Horticultural Society Colour Chart (The Royal Horticultural Society (R.H.S.), London, 2015 Edition. Where specific dimensions, sizes, colors, and other characteristics are given, it is to be understood that such characteristics are approximations or averages set forth as accurately as practicable.

Classification:

*Botanical name.*—*Spiraea* 'NCSX2'.

*Common name.*—*Spiraea* or *Spirea.*

Plant description:

*Habit.*—Rounded/mounded woody deciduous shrub.

*Height.*—80 to 100 cm.

*Width.*—80 to 100 cm.

Branches:

*Lateral branch diameter.*—About 0.3 cm.

*Lateral branch length.*—About 17.0 to 30.0 cm.

*Internode length.*—About 1.2 cm.

*Branch color.*—Immature: Greyed-Purple (183B). Mature: Greyed-Orange (165A).

*Branch texture.*—Exfoliating.

Leaves:

*Type.*—Simple.

*Persistence.*—Deciduous.

*Arrangement.*—Alternate.

*Shape.*—Ovate.

*Apex.*—Acute.

*Base.*—Acute.

*Venation.*—Pinnate.

*Vein color.*—Emerging leaves, upper and lower: Red-Purple (60B). Mature leaves, upper: Green (145A). Mature leaves, lower: Yellow-Green (145B).

*Margins.*—Serrate.

*Color.*—Newest Emerging leaves, upper and lower: Red (42A) Emerging leaves, upper and lower: Red-Purple (60B). Spring foliage: Yellow-Green 145B flushed Orange 26B. Mature leaves during the growing season (typically Summer), upper: Green (137A). Mature leaves during the growing season, lower: Greyed-Green (191A). Texture: Glabrous. Length of lamina: Avg. 6.0 cm (range 3.0 to 8.0 cm). Width: Avg. 3.0 cm (range 1.0 to 4.0 cm).

*Fall foliage color.*—Variable with some leaves turning a Light Yellow Green (145C), Moderate Yellow (162B), and/or Greyish Purple (N77A).

*Leaf attachment.*—Petiolate.

*Petiole.*—Length: 0.2 cm. Diameter: less than 0.1 cm. Color: Emerging leaves: Red-Purple (60B). Mature leaves: Yellow-Green (145A). Texture: Glabrous.

Inflorescence:

*Description.*—Single whorled, rotate flowers arranged on a terminal corymb.

*Number of true flowers per inflorescence.*—About 200.

*Flowering season.*—May through October in Mills River, N.C.

*Fragrance.*—Slight, sweet fragrance.

*Inflorescence diameter.*—16 cm (range 10 to 22 cm).

*Inflorescence height.*—11.8 cm (range 8.0 to 15.0 cm).

*Bud.*—Shape: Globular. Length: 0.3 cm. Diameter: 0.3 cm. Color: Red-Purple (59C).

*Perianth.*—Diameter: 0.8 cm. Height: 0.3 cm.

*Perianth aspect.*—Clustered, mostly outward facing.

*Petal.*—Arrangement: Whorl. Number: 5. Fused: Not fused. Texture: Glabrous. Shape: Globular. Margin: Entire. Apex: Obtuse. Base: Obtuse. Length: 0.2 cm. Width: 0.2 cm. Color when opening: Upper: Red-Purple (61B) to Red-Purple (N57B). Lower: Red-Purple (61C). Color at anthesis: Upper: Red-Purple (60C) to Red-Purple (N57B). Lower: Red-Purple (63B).

*Calyx.*—Shape: Cup-shaped with five lobes. Length: 0.2 cm. Diameter: 0.2 cm.

*Sepal.*—Arrangement: Single whorl. Number: 5. Texture: Pubescent. Shape: Acute. Margin: Entire. Apex: Acute. Base: Fused. Color: Yellow-Green (N148D) at base with Red-Purple (58A) at apex. Length: 0.3 cm. Width: 0.15 cm.

*Peduncle.*—Length: 0.52 cm (range 0.3 to 0.7 cm). Diameter: 0.05 cm. Color: Red-Purple (60B) fading to Greyed-Green (195B). Texture: Glabrous.

*Pedicels.*—Length: 0.26 cm (range 0.1 to 0.4 cm). Diameter: 0.05 cm. Color: Red-Purple (60B) fading to Greyed-Green (195B). Texture: Glabrous.

Reproductive organs:

*Gynoecium.*—Pistil number: 5. Pistil length: 0.2 cm. Stigma shape: Globose. Stigma color: Red-purple (60B). Style length: 0.5 mm. Style color: Red-Purple (60B). Ovary color: Red-Purple (60B).

*Androecium.*—Stamen number: 32. Anther shape: Globose. Anther size: 0.25 mm. Anther color: Black (202A). Filament length: 0.3 to 0.7 cm. Filament color: Red-Purple (61B). Amount of pollen: Very little. Pollen color: White (155D).

*Other.*—

Fruit and seed: None observed. Appears to be highly infertile.

DNA content: 2C DNA contend was determined following the methods of Shearer and Ranney (2013) using 4', 6-diamidino-2-phenylindole (DAPI) fluorochrome stain and *Pisum sativum* 'Ctirad' as an internal standard. Mean 2C DNA content for 'NCSX1' was 0.90 pg, which is consistent for a triploid based on research where 2C DNA contents for diploid *S. japonica* ranged from 0.52-0.61 pg (Wilson and Hoch, 2009).

Disease and insect resistance: Neither resistance nor susceptibility to normal diseases and pests has been observed.

Cold hardiness: At least USDA zone 5; testing has not been completed in colder zones.

What is claimed is:

1. A new and distinct hybrid *Spiraea* plant named 'NCSX2' substantially as illustrated and described herein.

* * * * *